United States Patent
Melamed et al.

(10) Patent No.: US 6,417,210 B1
(45) Date of Patent: Jul. 9, 2002

(54) TREATMENT OF DYSKINESIAS AND PARKINSON'S DISEASE WITH RILUZOLE AND LEVODOPA

(75) Inventors: Eldad Melamed, Tagore Street 44, Ramat Aviv, 69341 Tel Aviv; Ruth Djaldetti, Nathan Street 7, 52450 Ramat Gan; Ilan Ziv, Kfar-Sava, all of (IL)

(73) Assignees: MOR-Research Applications Ltd.; NST Neuro Survival Technologies Ltd.; Ruth Djaldetti, all of Petach Tikva; Eldad Melamed, Tel Aviv, all of (IL)

( * ) Notice: Subject to any disclaimer, the term of this patent is extended or adjusted under 35 U.S.C. 154(b) by 0 days.

(21) Appl. No.: 09/582,989

(22) PCT Filed: Jan. 5, 1999

(86) PCT No.: PCT/IL99/00003

§ 371 (c)(1), (2), (4) Date: Aug. 28, 2000

(87) PCT Pub. No.: WO99/34785

PCT Pub. Date: Jul. 15, 1999

(30) Foreign Application Priority Data

Jan. 9, 1998 (IL) ................................................ 122883
Nov. 17, 1999 (IL) ................................................ 127102

(51) Int. Cl.[7] ..................... A61K 31/425; A61K 31/195
(52) U.S. Cl. ........................................ 514/367; 514/567
(58) Field of Search ................................. 514/367, 567

(56) References Cited

U.S. PATENT DOCUMENTS 5,674,885 A * 10/1997 Boireau et al.

FOREIGN PATENT DOCUMENTS

| EP | 0 558 861 | 9/1993 |
|----|-----------|--------|
| WO | 94 15601  | 7/1994 |

OTHER PUBLICATIONS

Bensimon et al., "A Controlled Trial of Riluzole in Amyotrophic Lateral Sclerosis", *The New England Journal of Medicine*, (1994), vol. 330, No. 9, pp. 587–591.

Vidaluc, "MPTP as a Molecular Paradigm for Neurodegeneration. A Review of its Connections with Relevant Molecules", *Current Medicinal Chemistry*, (1996), vol. 3, pp. 117–138.

Palfi et al, "Riluzole Reduces Incidences of Abnormal Movement but Not Striatal Cell Death in a Primate Model of Progerssive Striatal Degeneration", *Experimental Neurology*, (1997), vol. 146, pp. 135–141.

XP–002094840, Rascol et al., "Pharmacologie clinique des dyskinésies induties par la L–Dopa chez lea malades parkinsoniens", *Théropie*, (1998), vol. 3, pp. 43–48.

XP–002094840, Starr et al., "Stimulation of Basal and L–DOPA–induced Motor Activities by Glutamate Antagonists in Animal Models of Parkinson's Disease", *Neuroscience and Biobehavioral Reviews*, (1997), vol. 21, No. 4, pp. 437–446.

XP–002109882, Barneoud et al, "Neuroprotective Effects of Riluzole on a Model of Parkinson's Disease in the Rat", *Neuroscience*, (1996), vol. 74, No. 4, pp. 971–983.

XP–002109883, Barneoud et al., "Neuroprotective Effects of Riluzole on a Model of Parkinson's Disease in the Rat", *Society of Neuroscience Abstracts*, (1995), vol. 21, No. 1–3, pp. 1256.

XP–002109884, Riluzole; Rilutek, *Drug Future*, (1996), vol. 21, No. 10, pp. 1077–1078.

XP–002109885, Doble, "Excitatory amino acid receptors and neurodegeneration", *Thérapie*, (1995), vol. 50, pp. 319–337.

XP–002109887, Richter et al., "Prodystomic effects of riluzole in an animal model of idiopathic dystonia related to decreased total power in the red nucleus", *European Journal of Pharmacology*, (1997), vol. 332, pp. 133–141.

XP–002109888, Kiel, "Schlusselfunktion von Glutamat im Netzwerk neurodegenerativer Prozesse", *Pharmazie & Technik*, (1998), vol. 4, No. 6, pp. 326–327.

XP–002109889, Imperator et al., "Riluzole Prevents Dyskinesias in Parkinsonian Marmosets, Behavior and Histology", *Society for Neuroscience Abstracts*, (1998), vol. 24, No. 1–2, pp. 763.

XP–002109890, Abstract, Palfi et al., "New experimental therapies for the treatment of motor and cognitive deficits in Huntington's disease", (1997).

XP–002109891, Abstract, Hassani, "Controle Dopaminergique Du Noyau Subthalamique Chez Le Rat Normal Et Chez Le Rate Modele De La Maladie De Parkinson (Rats 6–OHDA)", (1997).

XP–000600898, Benazzouz et al., "Riluzole prevents MPTP–induced Parkinsonism in the rhesus monkey; a pilot study", *European Journal of Pharmacology*, (1995), vol. 284, pp. 299–307.

* cited by examiner

*Primary Examiner*—William R. A. Jarvis
(74) *Attorney, Agent, or Firm*—Browdy and Neimark

(57) ABSTRACT

This invention relates to pharmaceutical compositions of riluzole in combination with levodopa and methods of treating Parkinson's disease and alleviating levodopa-induced dyskinesia and tardive dyskinesia therewith. Pharmaceutical compositions of riluzole in combination with an antipsychotic drug are also provided for use in the treatment of behavioral and psychiatric disorders treatable with an antipsychotic drug.

14 Claims, No Drawings

TREATMENT OF DYSKINESIAS AND PARKINSON'S DISEASE WITH RILUZOLE AND LEVODOPA

CROSS REFERENCE TO RELATED APPLICATION

The present application is the national stage under 35 U.S.C. 371 of PCT/IL99/00003, filed Jan. 5, 1999.

FIELD OF THE INVENTION

The present invention concerns pharmaceutical compositions for the treatment of levodopa-induced dyskinesia and tardive dyskinesia.

BACKGROUND OF THE INVENTION

Parkinson's disease is an age related, progressive neurodegenerative disorder. The prevalence rate is approximately 0.5% in the population aged 50–59, 1% in ages 60–69, 2% in the 70–79 age group and rises to over 3% in those who are 80 and older. Prevalence rates are similar in Europe.

Parkinson's disease is characterized by a relatively selective degeneration of dopaminergic neurons in the substantia nigra pars compacta with loss of striatal dopamine. The pathology shows depigmentation of the substantia nigra and intracellular inclusions (Lewy bodies). The cardinal features of the disease include resting tremor, rigidity, bradykinesia and postural instability. Current treatment of the motor signs of Parkinson's disease is based on dopamine replacement. This involves the administration of levodopa, usually combined with a decarboxylase inhibitor. Exogenous levodopa is converted in the striatum to dopamine and replenishes the reduced dopaminergic concentrations in the basal ganglia. Dopamine agonists may be helpful as well. During the first years of treatment the patients enjoy a smooth and stable response to this treatment. However, after 2–5 years of chronic treatment with dopaminergic preparations, 75% of patients develop disabling and incapacitating motor complications. One of the most common side effects is the levodopa-induced dyskinesias (choreiform and dystonic involuntary movements). They occur in the majority (80–100%) of the patients as their illness progresses. Dyskinesias may be initially mild but they can become more and more progressive, complex, generalized, violent, and may severely interfere with motor function, speech, coordination and postural stability. Patients and families are often shameful by the unaesthetic and bizarre movements which can affect facial muscles, eyelids, mouth, cheeks, lips and tongue, upper and lower limbs and even trunk and respiratory muscles. This is one of the major reasons for social decline of afflicted patients.

At the beginning, when they first emerge, dyskinesias are mainly the peak-dose type, i.e., they are most prominent when levodopa plasma levels are high. When patients later develop response fluctuations after chronic levodopa treatment, dyskinesias may also appear at the beginning and again at the termination of an individual levodopa dose beneficial effect. When disease is more advanced, dyskinesias predominate in an "all or none" fashion, i.e., they are present throughout the duration of an "on" period, induced by a successful single oral dose of levodopa. Such levodopa-induced dyskinesias also represent a major limiting factor in the pharmacological treatment of Parkinson's disease.

When their illness progresses, the patients need increases in their daily levodopa dosage and the addition of other dopaminergic agents, e.g., dopamine agonists and MAO-B inhibitors. This is invariably associated with a rapid and intolerable increase of the frequency, distribution and severity of dyskinesias necessitating reduction of drugs. Dyskinesias are probably and primarily caused by the action of excessive exogenous dopamine on denervation-supersensitive post-synaptic dopaminergic receptors. Normally, the dopamine formed from levodopa is stored in vesicles within the dopaminergic nerve-endings for regulated release into the synapse. As the disease progresses, more nigral dopaminergic neurons degenerate and there is more severe loss of their nerve-terminals in the basal ganglia (caudate and putamen nuclei).

It is believed that the decarboxylation of exogenous levodopa therefore shifts to non-dopaminergic striatal compartments. Since the generated dopamine molecules are not stored, they immediately interact and hyperactivate the postsynaptic dopaminergic receptors (mainly of the D2 subtype) resulting in the involuntary movements. There is no satisfactory treatment for this type of dyskinesia. Discontinuation or reduction of levodopa and other dopaminergic drugs or addition of neuroleptic drugs that block dopaminergic receptors, can abolish the abnormal movements, but at the expense of severe aggravation of the parkinsonian symptoms. The control-release levodopa preparations have been proven unhelpful. This despairing state of affairs suggested that it would be difficult if not impossible to dissociate the beneficial anti-parkinsonian from the bad dyskinetic producing effects of levodopa.

Behavioral and psychiatric disorders are usually treated administration of by various anti-psychotics, also termed: "neuroleptic drugs", the majority of which act by blockage of dopamine $D_2$ receptor. Prolonged administration of antipsychotic drugs often results in development of involuntary movements, termed: "tardive dyskinesia".

Riluzole (2-amino-6-trifluoromethoxy benzothiazole) has recently emerged as a pharmacological agent potentially useful to slow down the evolution of neurodegenerative diseases, such as amyotrophic later,a sclerosis. (Ben Simon et al., *New Engl. J. Med.*, 330:585–91 (1994)). In addition, this molecule has been shown to display anticonvulsant, anti-ischemic, and neuroprotective properties under various experimental conditions. A clear understanding of the site and mechanism of action of this molecule is still lacking.

There has been recently a report (Palfi et al. *Exper. Neurol* 146 135–141 (1997)) that riluzole reduces various abnormal motor movement in baboons which were induced by 3-nitropropionic acid, serving as a model for progressive striatal degeneration, which is a model for Huntington's disease.

SUMMARY OF THE INVENTION

The present invention provides, by one of its aspects, a pharmaceutical composition for the amelioration of levodopa-induced dyskinesia and tardive dyskinesia, comprising as an active ingredient, a pharmaceutically effective amount of riluzole.

The present invention provides, by another of its aspects, use of riluzole for the preparation of a pharmaceutical composition for the amelioration of levodopa-induced dyskinesia and tardive dyskinesia.

The term "amelioration" refers to a decrease in the abnormal involuntary movements characterizing these two types of dyskinesia, as can be determined for example, by using the Abnormal Involuntary Movement Scale (AIMS) as will be specified hereinbelow.

The term "levodopa-induced dyskinesia" refers to dyskinesia, i.e. involuntary choreiform movements, brought about by the chronic administration of levodopa, for example in patients suffering from Parkinson's disease.

The term "tardive dyskinesia" refers to dyskinesia brought about by the chronic administration of neuroleptic, anti-psychotic drugs of the Dopaminergic-receptor blocker type.

The term "riluzole" refers to 2-amino-6 trifluoromethoxy-benzothiazole.

The term "effective amount" refers to an amount that brings about to a reduction in the AIMS of the patients without causing severe side effects.

The dosage of the active ingredient should be tested empirically for each specific indication, and depends on various factors, such as the patient's weight, the length of time of administration of the levodopa or the neuroleptic pharmaceutical composition, age, etc. Generally speaking, the dosage should be of about 25 to about 200 mg per day, preferably of about 50 to about 200 mg per day, most preferably of about 50 to about 100 mg per day.

The pharmaceutical composition of the invention, may comprise olely riluzole and a pharmaceutically acceptable carrier.

Alternatively, it is possible to include in one dosage form, both the dyskinesia causing agent such as the neuroleptic drug (in the case of tardive dyskinesia), or levodopa (in the case of levodopa-induced dyskinesia) together with the riluzole.

The present invention further concerns a method for ameliorating levodopa-induced dyskinesia or tardive dyskinesia by administering to a subject in need of such treatment, a therapeutically effective amount of riluzole.

According to the-method of the present invention, the riluzole may be administrated separately, i.e. not simultaneously with the dyskinesia-causing agent (such as the neuroleptic drug or the levodopa), or alternatively may be administered together with the dyskinesia-causing agents either by administration of the two medicaments simultaneously or by forming both medicaments in a single dosage form.

The invention will now be described with reference to some non-limiting examples.

DETAILED DESCRIPTION OF THE INVENTION

I. Clinical Procedures

Twelve patients suffering from advanced Parkinson's disease featuring dyskinesia, and twelve patients having appropriate criteria for tardive dyskinesia are participating in an open experiment for assessing the influence of riluzole on involuntary movement.

The Parkinson patients are balanced by optimal dopaminergic treatment in the three months prior to the clinical trial. The patients with tardive dyskinesia, which are already balanced by neuroleptic treatment, do not reduce the dosage of the neuroleptic drug and do not cease other treatments, which they receive.

The clinical assessment of the Parkinson patient is carried out by using the Unified Parkinson's Disease Rating Scale (UPDRS) and the assessment of involuntary movement will be carried out by the Abnormal Involuntary Movement Scale (AIMS).

Assessment of patients with tardive dyskinesia is carried out utilizing AIMS. The trial is carried out for six weeks. Prior to the beginning of the trial, patients undergo blood and urine tests, a chest X-ray, an ECG, as well as general physical and neurological evaluations. During the clinical trial, the patients are treated with riluzole having an initial dosage of 25 mg. twice a day, and after a week, the dosage will be increased to 50 mg. twice a day. Patients are monitored once every two weeks in order to carry out a blood count and SMA (biochemical blood tests). In addition, a clinical assessment-involuntary-movement is carried out separately by two independent physicians. During the clinical trial, patients are asked to fill a detailed diary which will grade the severity of the dyskinesia and will assess daily function according to the following scale:

THE INTENSITY OF THE DYSKINESIA 0-without dyskinesia
1-mild dyskinesia
2-medium dyskinesia,
3-severe dyskinesia

RATING OF DAILY FUNCTION

1-An improvement of daily function as compared to the basic condition
2-No improvement in daily function
3-Deterioration of daily function as compared to the basic condition At the end of the clinical trial, patients undergo blood tests, ECG's, as well as neurological and psychological assessment.

In addition, patients are invited for routine check-ups two weeks from the end of the trial.

II. Clinical trials

Six patients suffering from advanced Parkinson's disease with severe levodopa-induced dyskinesias participated in an open-label pilot study to assess safety, tolerability and efficacy of riluzole in attenuating the involuntary movements.

The patients were given optimal anti-parkinsonian drug treatment during the three months prior to the clinical trial. Duration of study was six weeks. First two weeks served to accumulate baseline data. Patients filled up dyskinesias diaries in which they marked at every waking hour whether involuntary movements were present and their severity (mild/moderate and severe). Each patient was administered with half a tablet of riluzole (25 mg) once, in the morning, for four days. The dose was then increased to 25 mg, b.i.d. for additional four days (once in the morning and once in the early afternoon). The dose as then further increased to two 50 mg tablets (total of 100 mg. daily) which the patients took for three additional weeks. They continued to fill up their dyskinesias diaries throughout the trial period.

Results

Treatment with riluzole was found to be effective in attenuating the dyskinesias. Mean daily waking hours spent with dyskinesias decreased by about 24% from 6.92±3.67 hours before treatment to 5.26±4.23 hours during treatment ($P<0.01$; paired t-test). Mean daily waking hours spent in severe dyskinesias reduced by about 30% from 2.76±1.77 hours before treatment to 1.94±2.40 hours during treatment with riluzole ($0.01<p<0.05$; paired t-test). There was no worsening of the parkinsonian signs and symptoms when patients took riluzole. Likewise, there was no decrease in the efficacy of levodopa and other anti-parkinsonian drugs and in the total daily time patients spent in "on" periods.

Riluzole was well-tolerated and there was no report of adverse-effects. This preliminary open-label study indicates that administration of riluzole (50 mg. b.i.d) can attenuate levodopa-induced dyskinesias in patients with Parkinson's disease without causing deterioration of the parkinsonian signs and without suppression of levodopa efficacy.

What is claimed is:

1. A pharmaceutical composition for the treatment of Parkinson's disease comprising an effective amount of riluzole in combination with an effective amount of levodopa and a pharmaceutically acceptable carrier.

2. A pharmaceutical composition according to claim 1 comprising about 25 to about 200 mg of riluzole.

3. A pharmaceutical composition according to claim 1, comprising about 50 to about 100 mg of riluzole.

4. A pharmaceutical composition comprising an antipsychotic drug, an effective amount of riluzole, and a pharmaceutically acceptable carrier.

5. A pharmaceutical composition according to claim 4, comprising about 25 to about 200 mg of riluzole.

6. A method for ameliorating levodopa-induced dyskinesia or tardive dyskinesia comprising administering to a subject in need of such treatment, a therapeutically effective amount of riluzole.

7. A method according to claim 6, wherein the riluzole is administered in an amount of about 25 to about 200 mg per day.

8. A method according to claim 7, wherein the riluzole is administered in an amount of about 50 to 200 mg per day.

9. A method according to claim 8, wherein the riluzole is administered in an amount of about 50 to 100 mg per day.

10. A method for the treatment of Parkinson's disease comprising administering to a subject in need of such treatment riluzole and levodopa.

11. A method according to claim 10, wherein the riluzole is administered in an amount of about 25 to about 200 mg per day.

12. A method according to claim 11, wherein the riluzole is administered in an amount of about 50 to about 100 mg per day.

13. A method for the treatment of behavioral and psychiatric disorders treatable with an antipsychotic drug, comprising administering to a subject in need of such treatment said anti-psychotic drug and riluzole.

14. A method according to claim 13, wherein the riluzole is administered in an amount of about 25 to about 200 mg per day.

* * * * *